United States Patent
Ten Kate (10) Patent No.: US 9,489,815 B2
(45) Date of Patent: Nov. 8, 2016

(54) APPARATUS FOR USE IN A FALL DETECTOR OR FALL DETECTION SYSTEM, AND A METHOD OF OPERATING THE SAME

(75) Inventor: Warner Rudolph Theophile Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/114,592

(22) PCT Filed: Nov. 4, 2011

(86) PCT No.: PCT/IB2011/054934
§ 371 (c)(1),
(2), (4) Date: Feb. 24, 2014

(87) PCT Pub. No.: WO2012/146957
PCT Pub. Date: Nov. 1, 2012

(65) Prior Publication Data
US 2014/0191863 A1    Jul. 10, 2014

(30) Foreign Application Priority Data

Apr. 29, 2011  (EP) .................................... 11164240

(51) Int. Cl.
*G08B 1/08* (2006.01)
*G08B 21/02* (2006.01)
*A61B 5/11* (2006.01)
*G08B 21/04* (2006.01)
(Continued)

(52) U.S. Cl.
CPC ............ *G08B 21/02* (2013.01); *A61B 5/02055* (2013.01); *A61B 5/1116* (2013.01); *A61B 5/1117* (2013.01); *A61B 5/1126* (2013.01); *A61B 5/7203* (2013.01); *A61B 5/725* (2013.01); *A61B 5/7275* (2013.01); *A61B 5/7282* (2013.01); *G08B 21/0446* (2013.01); *G08B 21/0453* (2013.01); *H04M 3/5116* (2013.01); *A61B 5/021* (2013.01); *A61B 5/02438* (2013.01); *A61B 5/0531* (2013.01); *A61B 5/1102* (2013.01); *A61B 5/14551* (2013.01); *A61B 5/747* (2013.01); *A61B 2562/0219* (2013.01); *H04M 2250/12* (2013.01)

(58) Field of Classification Search
CPC .............. A61B 5/1117; A61B 5/1116; G08B 21/0446; G08B 21/0453
USPC .................. 340/539.12, 686.1, 689; 600/483
See application file for complete search history.

(56) References Cited

U.S. PATENT DOCUMENTS

| | | | |
|---|---|---|---|
| 6,160,478 | A | 12/2000 | Jacobson et al. |
| 2003/0153836 | A1 | 8/2003 | Gagnardre et al. |

(Continued)

FOREIGN PATENT DOCUMENTS

| | | | |
|---|---|---|---|
| FR | 2883093 | A1 | 9/2006 |
| FR | 2912049 | A1 | 8/2008 |

(Continued)

*Primary Examiner* — John A Tweel, Jr.

(57) ABSTRACT

There is provided a method of operating a fall detector, the method comprising, on detecting a fall event by a user of the fall detector, measuring at least one physiological characteristic of the user; and using the measurement of the at least one physiological characteristic to determine whether to expedite an alert that the user has fallen. An apparatus comprising a processor that is configured to perform the method described above is also provided.

20 Claims, 3 Drawing Sheets

(51) Int. Cl.
  *A61B 5/0205* (2006.01)
  *H04M 3/51* (2006.01)
  *A61B 5/053* (2006.01)
  *A61B 5/00* (2006.01)
  *A61B 5/021* (2006.01)
  *A61B 5/024* (2006.01)
  *A61B 5/1455* (2006.01)

(56) References Cited

U.S. PATENT DOCUMENTS

| | | |
|---|---|---|
| 2005/0206506 A1 | 9/2005 | Kulesz et al. |
| 2007/0033194 A1 | 2/2007 | Srinivas et al. |
| 2007/0063850 A1* | 3/2007 | Devaul et al. ............ 340/573.1 |
| 2008/0084296 A1 | 4/2008 | Kutzik et al. |
| 2009/0040052 A1 | 2/2009 | Cameron et al. |
| 2010/0261984 A1 | 10/2010 | Tsai et al. |
| 2010/0286490 A1 | 11/2010 | Koverzin |
| 2011/0025493 A1 | 2/2011 | Papadopoulos et al. |
| 2011/0111736 A1 | 5/2011 | Dalton et al. |

FOREIGN PATENT DOCUMENTS

| | | | |
|---|---|---|---|
| GB | 2401466 A | 11/2004 | |
| JP | 2002360522 A | 12/2002 | |
| JP | 2005278765 A | 10/2005 | |
| JP | 2006341062 A | 12/2006 | |
| JP | 2009301457 A | 12/2009 | |
| WO | 0185025 A1 | 11/2001 | |
| WO | 0235997 A1 | 5/2002 | |
| WO | 2004114245 A1 | 12/2004 | |
| WO | 2007022084 A2 | 2/2007 | |
| WO | 2007033194 A2 | 3/2007 | |
| WO | 2007100959 A2 | 9/2007 | |

* cited by examiner

APPARATUS FOR USE IN A FALL DETECTOR OR FALL DETECTION SYSTEM, AND A METHOD OF OPERATING THE SAME

CROSS-REFERENCE TO PRIOR APPLICATIONS

This application is the U.S. National Phase application under 35 U.S.C. §371 of International Application Serial No. PCT/IB2011/054934, filed on Nov. 4, 2011, which claims the benefit of Application Serial No. 11164240.1, filed on Apr. 29, 2011. These applications are hereby incorporated by reference herein.

TECHNICAL FIELD OF THE INVENTION

The invention relates to an apparatus for use in a fall detector or a fall detection system that detects falls by a user and triggers an alert when a fall occurs in order to get help for the user, and a method of operating the same.

BACKGROUND TO THE INVENTION

Falls affect millions of people each year and result in significant injuries, particularly among the elderly. In fact, it has been estimated that falls are one of the top three causes of death in elderly people. A fall is defined as a sudden, uncontrolled and unintentional downward displacement of the body to the ground or a lower level, followed by contact (such as an impact) with the ground or lower level, after which the body stays down on the ground.

Personal Help Buttons (PHBs) are available that require the user to push the button to summon help in an emergency. When pressed, the PHB initiates a call to a call centre and then allows the user to communicate with call centre staff who will arrange for help to be sent to the user as required. However, if the user suffers a severe fall (for example if they are knocked unconscious), the user might be unable to push the button, which might mean that help doesn't arrive for a significant period of time, particularly if the user lives alone or if no-one witnesses the user fall.

PHBs have therefore been improved to include one or more movement sensors whose measurements are processed in order to detect a fall by the user and to trigger a call without the user having to press the button on the PHB. Most existing fall detectors make use of an accelerometer (usually an accelerometer that measures acceleration in three dimensions) and they try to infer the occurrence of a fall by processing the time series generated by the accelerometer. Some fall detectors can also include an air pressure sensor, for example as described in WO 2004/114245. The detection algorithms are typically designed for low power consumption, such that there is no need for frequent battery replacement or recharging. In addition, in some fall detectors, an alert is only triggered or initiated if the user does not stand up within a predetermined time period following a detected fall (sometimes referred to as the "revocation period").

The use of a revocation period introduces a delay between a fall event occurring, and contact being made with the call centre. Typically, the revocation period is about 20 to 30 seconds, although it can be set to a different value. Furthermore, depending on the actual number of incoming calls at the call centre when the emergency call is triggered, the call may be placed in a queue, further delaying the dispatch of help to the user. For someone who has fallen and urgently requires help, any delay can significantly affect their chances of survival.

The delay can also be serious if the fall has been caused by some underlying health-related issue. For example, if there has been a failure in the user's vital system, such as a stroke or a cardiac arrest, then any delay in receiving emergency help can have significant consequences for the user.

Therefore, there is a need for an improved fall detector or fall detection system and a method of operating the same that overcomes the problems with the use of a revocation period. More generally, there is a need for an improved fall detector or fall detection system and method of operating the same in which the time taken to get help to a user who has suffered a fall can be reduced if that user is urgently in need of help.

SUMMARY OF THE INVENTION

According to a first aspect of the invention, there is provided a method of operating a fall detector, the method comprising, on detecting a fall event by a user of the fall detector, measuring at least one physiological characteristic of the user; and using the measurement of the at least one physiological characteristic to determine whether to expedite an alert that the user has fallen.

In a preferred embodiment, the step of using the measurement of the at least one physiological characteristic to determine whether to expedite an alert that the user has fallen comprises determining if the measurement of the at least one physiological characteristic deviates from a normal value for the at least one physiological characteristic; and expediting an alert that the user has fallen if the at least one physiological characteristic deviates from a normal value for the at least one physiological characteristic.

In some embodiments, the step of using the measurement of the at least one physiological characteristic to determine whether to expedite an alert that the user has fallen further comprises, otherwise, issuing a non-expedited alert that the user has fallen.

In other embodiments, the step of using the measurement of the at least one physiological characteristic to determine whether to expedite an alert that the user has fallen further comprises, if the at least one physiological characteristic does not deviate from a normal value for the at least one physiological characteristic, initiating an alert that the user has fallen if it is determined that the user has not got up within a predetermined time period after the detected fall event.

Preferably, the step of determining if the measurement of the at least one physiological characteristic deviates from a normal value for the at least one physiological characteristic comprises comparing the measurement of the at least one physiological characteristic to a threshold value or a normal range of values for the at least one physiological characteristic.

In some embodiments, the normal value for the at least one physiological characteristic is user-dependent.

The method can further comprise the steps of measuring the movements of the user; and analyzing the measured movements to identify one or more movements indicative of a fall by the user. The one or more movements consistent with a fall can be selected from an impact, a change in height of the user, a vertical velocity and a change in orientation of the user.

In preferred embodiments, the measured movements are further analyzed to obtain the measurement of the at least one physiological characteristic of the user. In alternative embodiments, the step of measuring at least one physiological characteristic of the user comprises using a sensor different to that used to measure the movements of the user.

An alert can comprise at least one of an audible alarm, a call to a call centre, emergency service or nominated recipient or sending data to a call centre, emergency service or nominated recipient. Expediting an alert can comprise one or more of initiating an alert before the expiry of a revocation period, labeling a call or message as high priority such that queuing of the call or message at a recipient is expedited compared to a non-expedited alert, initiating an alert through a higher priority or higher bandwidth channel in a network than a non-expedited alert, initiating an alert to an emergency service instead of, or in addition to, a call centre associated with the fall detector.

The at least one physiological characteristic can be selected from heart rate, heart rate variability, respiration rate, respiration rate variability, body temperature, skin conductivity and blood pressure.

According to a second aspect of the invention, there is provided a computer program product comprising computer readable code embodied therein, the code being configured such that, on execution by a suitable computer or processor, the computer or processor is caused to perform the method as described above.

According to a second aspect of the invention, there is provided an apparatus, comprising a processing unit that is configured to determine a measurement of at least one physiological characteristic of a user of a fall detector on detecting a fall event by the user; and use the measurement of the at least one physiological characteristic to determine whether to expedite an alert that the user has fallen.

In a preferred embodiment, the processor is configured to determine that an alert should be expedited if the at least one physiological characteristic deviates from a normal value for the at least one physiological characteristic.

The processor can be further configured to issue a non-expedited alert that the user has fallen if otherwise.

Alternatively, the processor can be configured such that, on determining that the at least one physiological characteristic does not deviate from a normal value for the at least one physiological characteristic, the processor initiates an alert that the user has fallen if it is determined that the user has not got up within a predetermined time period after the detected fall event.

Preferably, the processor can be configured to determine if the measurement of the at least one physiological characteristic deviates from a normal value for the at least one physiological characteristic by comparing the measurement of the at least one physiological characteristic to a threshold value or a normal range of values for the at least one physiological characteristic.

Preferably, the processor can be configured to receive measurements of the movements of the user and to analyze the movement measurements to identify one or more movements indicative of a fall by the user.

In some embodiments, the processor can be configured to further analyze the measured movements to obtain the measurement of the at least one physiological characteristic of the user.

In alternative embodiments, the processor can be configured to receive measurements of the at least one physiological characteristic of the user from a sensor different to that from which the measurements of the movements of the user are received.

In some embodiments, the processor can be configured to issue an alert selected from an audible alarm, a call to a call centre, emergency service or nominated recipient or sending data to a call centre, emergency service or nominated recipient.

In some embodiments, the processor can be configured to expedite an alert by initiating an alert before the expiry of a revocation period, labeling a call or message as high priority such that queuing of the call or message at a recipient is expedited compared to a non-expedited alert, initiating an alert through a higher priority or higher bandwidth channel in a network than a non-expedited alert, initiating an alert to an emergency service instead of, or in addition to, a call centre associated with the fall detector.

According to another aspect of the invention, there is provided a fall detector that is configured to be worn by a user, the fall detector comprising an apparatus as described above.

The fall detector can further comprise a movement sensor for measuring the movement of the user. The movement sensor can comprise at least one of an accelerometer, an air pressure sensor, an air flow sensor, a magnetometer and a gyroscope.

The fall detector can further comprise at least one physiological characteristic sensor. The at least one physiological characteristic sensor can comprise at least one of a heart monitor, a breathing rate monitor, a photoplethysmograph (PPG), a blood pressure sensor, a thermometer and a skin conductivity sensor.

According to a further aspect of the invention, there is provided a fall detection system, comprising a sensor unit that is configured to be worn by a user; and a base unit that is configured to communicate with the sensor unit, and that comprises an apparatus as described above.

The sensor unit can further comprise a movement sensor for measuring the movement of the user. In some embodiments, the movement sensor comprises at least one of an accelerometer, an air pressure sensor, an air flow sensor, a magnetometer and a gyroscope.

The sensor unit can further comprise at least one physiological characteristic sensor. The physiological characteristic sensor can comprise at least one of a heart monitor, a breathing rate monitor, a photoplethysmograph (PPG), a blood pressure sensor, a thermometer and a skin conductivity sensor.

Thus, the invention provides a fall detector or fall detection system that uses a measurement of one or more physiological characteristics following a detected fall event to determine whether to expedite an alert that the user has fallen and requires assistance. Furthermore, in preferred embodiments, as the physiological characteristic monitoring is only triggered when a fall has been detected, the power consumption of the fall detector or sensor unit in a fall detection system can be minimized.

BRIEF DESCRIPTION OF THE DRAWINGS

Embodiments of the invention will now be described, by way of example only, with reference to the following figures, in which.

DETAILED DESCRIPTION OF THE PREFERRED EMBODIMENTS

Figure 1:
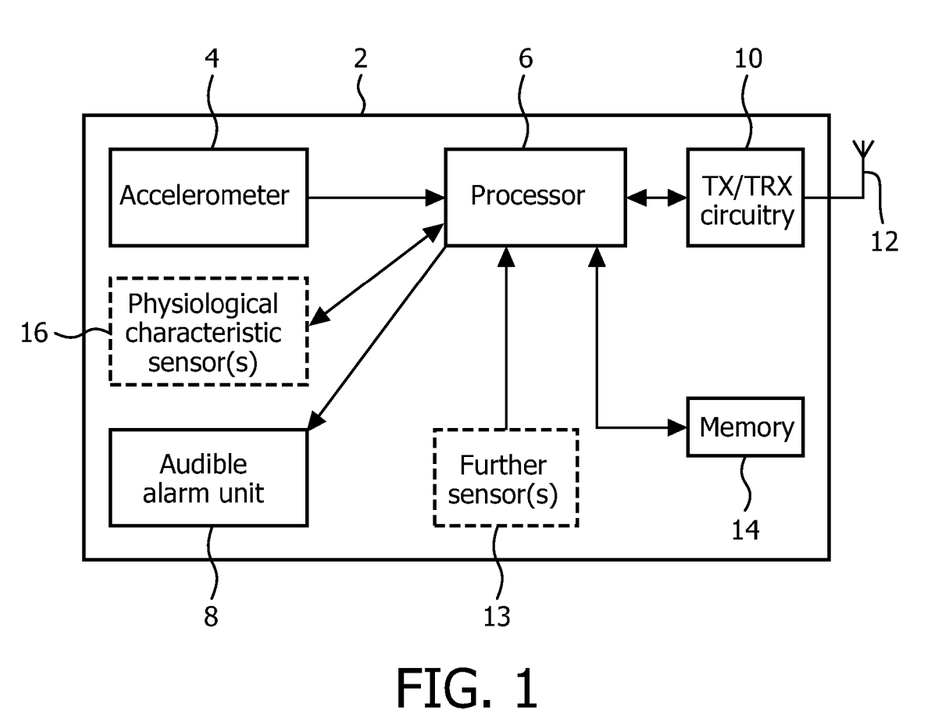
FIG. 1 is a block diagram of a fall detector according to an embodiment of the invention.

FIG. 1 illustrates an exemplary fall detector 2 in accordance with an embodiment of the invention. The fall detector 2 is in the form of a sensor unit that is to be worn by a user. The fall detector 2 can be provided in the form of a pendant with a neck cord for placement around the user's neck, but alternatively the fall detector 2 can be configured to be worn at or on a different part of the user's body, such as the wrist, waist, trunk, pelvis or sternum, and will comprise a suitable arrangement for attaching the fall detector 2 to that part of the body (for example a belt or a strap).

The fall detector 2 is used to measure the movement of the user (for example the accelerations experienced by the user) and to process the measurements to determine whether the user has fallen.

The fall detector 2 comprises a movement sensor 4 for measuring the movement of the user. The movement sensor 4 is preferably an accelerometer 4, and is preferably an accelerometer 4 that measures acceleration along three orthogonal axes. The signals output by the accelerometer 4 are provided to a processor 6 for analysis. In some embodiments, the accelerometer 4 is a micro-electromechanical system (MEMS) accelerometer. The acceleration experienced by the accelerometer 4 can be sampled at a rate of 30 Hz, although it will be appreciated that many other sampling frequencies can be used (for example 50 or 100 Hz).

The fall detector 2 comprises one or more components for use in issuing an alert in order to obtain help for the user of the fall detector 2. As illustrated, one of the components can be an audible alarm unit 8 that can be triggered by the processor 6 if a fall is detected. This alarm can summon help to the user by alerting anyone in the vicinity of the user. However, it will be appreciated that the presence of an audible alarm unit in the fall detector 2 is optional. A further optional component is a help button (not shown in FIG. 1) that can be pressed by a user to summon help.

Another component that can be used in issuing an alert is transmitter or transceiver circuitry 10 in conjunction with antenna 12. The transmitter or transceiver circuitry 10 and associated antenna 12 can be used to place an emergency call over a wired or wireless telephone network (or other type of network, such as the Internet) to a call centre or nominated person to summon help in the event that a fall is detected or in the event that a help button (if present) has been pressed. The circuitry 10 or additional circuitry (such as that based on infra-red or other short-range wireless technologies such as Bluetooth) can also be used to transmit the results of the processing to a remote (base) unit.

The fall detector 2 may also contain one or more further sensors 13 for measuring the movement and/or posture of the user, the measurements from which can be used by the processor 6 in conjunction with the measurements from the accelerometer 4 to determine whether the user has suffered a fall. The further sensor(s) 13 can comprise, for example, a gyroscope, a magnetometer, an air pressure sensor and/or an air flow sensor.

The fall detector 2 also optionally comprises a memory 14 that can be used for storing measurements from the accelerometer 4 (and the further sensors 13, if present in the fall detector 2), the results of the processing by the processor 6 and program code that contains instructions for causing the processor 6 to operate according to the invention.

As described in more detail below, the invention provides that at least one physiological characteristic of the user is measured when a fall or a possible fall has been detected, and this measurement can be used to determine whether to expedite an alert that the user has fallen. In particular, if the measured physiological characteristic is not normal or within a normal range, then an alert that the user has fallen can be expedited since the physiological characteristic indicates that the user urgently requires assistance. However, if the measured physiological characteristic is normal or within a normal range, then an alert that the user has fallen can be initiated in the 'normal' way (i.e. non-expedited).

Alerts can typically comprise the placing a call over a wired or wireless telephone network (or other type of network, such as the Internet) to a call centre or nominated person, transmitting data (including the sending of an SMS message) indicating that the user has fallen to a call centre, activating an audible alarm unit 8 in the detector 2 or another device, such as a base unit for the fall detector 2, or any other suitable type of alert.

These alerts can be expedited in a number of different ways. For example, where the fall detector makes use of a revocation period in order to determine if the user gets up following a fall, expediting the alert can comprise triggering or initiating the alert immediately, rather than awaiting the expiry of the revocation period.

Another way in which an alert can be expedited is to include a priority label in the call or message signaling, where this priority label can be read at the call centre or by any other recipient and used to accelerate the processing of the call or message (for example by placing the call at the top of a queue in a call centre queuing system or by placing the call into a different queue to that normally used to handle fall detector-initiated calls). In addition, or alternatively, this priority label can be used to expedite the handling of the call signaling through the telephone or other network (for example by allocating the signaling to a channel in the network with higher bandwidth).

Yet another way in which an alert can be expedited is for the call to be placed to an emergency service (e.g. 911 or 999) rather than (or in addition to) the call centre associated with the fall detector to which a call would normally be placed or message sent.

It will be appreciated that expediting an alert can also include other related actions and using combinations of them and the techniques described above.

The physiological characteristic(s) measured can be any characteristic that might provide information that is useful for determining the status of the user following a fall, such as a heart rate, heart rate variability, breathing rate, blood pressure, skin conductivity, body temperature, etc.

In advantageous embodiments of the invention, the at least one physiological characteristic is measured using one or more of the movement sensors already present in the fall detector 2 (for example the accelerometer 4). This means that it is not necessary to include additional sensors in the fall detector 2. For example, a pulse (heart beat) will appear as peaks in the signal from the accelerometer 4, due to ballistic body movements in response to the pumping blood flow as well as due to the heart's movement itself A respiration rate will appear as a slight orientation change (represented as a change in the measured direction of gravity), caused by movements of the user's chest or abdomen.

In alternative embodiments, the fall detector 2 can comprise one or more separate physiological characteristic sensor(s) 16 (which are shown as an optional feature in FIG. 1). These physiological characteristic sensor(s) 16 can include a heart monitor, a breathing rate monitor, a photoplethysmograph (PPG), a blood pressure monitor, a skin conductivity sensor, a thermometer, an ECG, an EMG, etc. In some embodiments, one or more of the physiological characteristic sensor(s) 16 can be provided in a separate housing or component to that containing the movement sensor 4. For example, the fall detector 2 can be configured as a pendant to be worn around the user's neck which contains the accelerometer 4 and the processor 6, and a skin conductivity sensor 16 can be provided in a separate wristband. In this case, means can be provided to provide the measurements from the skin conductivity sensor 16 to the processor 6 in the pendant for processing.

The separate sensor component may also include a processor that can determine a physiological characteristic from the measurement. The sensor component may also include transceiver circuitry for initiating an alert if the characteristic is not a normal value. The fall detector 2 can be configured to communicate with the separate sensor component and request measurements be performed. The outcome of the measurement can be returned to the fall detector 2, or the separate sensor component can decide to initiate an alert itself.

It will be appreciated that only components of the fall detector 2 that are required for explaining the invention have been illustrated in FIG. 1, and a fall detector 2 according to the invention may include further components and functionality to those described herein. For example, it will be appreciated that a fall detector 2 will include some form of power source or supply and circuitry for controlling the operation of the fall detector 2.

In an alternative embodiment to that illustrated, a fall detection system can be provided in which the processing of the movement sensor measurements (and physiological characteristic sensor measurements, if appropriate) is performed in a base unit that is separate to a sensor unit (that corresponds in structure to fall detector 2 shown in FIG. 1) that is worn by the user. In that case, the movement sensor measurements (and physiological characteristic sensor measurements, if appropriate) can be transmitted from the sensor unit 2 to the base unit via the transceiver circuitry 10. In a further alternative embodiment, the sensor unit 2 may perform some of the initial processing steps on the movement sensor measurements before transmitting the results to a base unit which, for example, completes the processing and determines whether the user has fallen.

Figure 2:
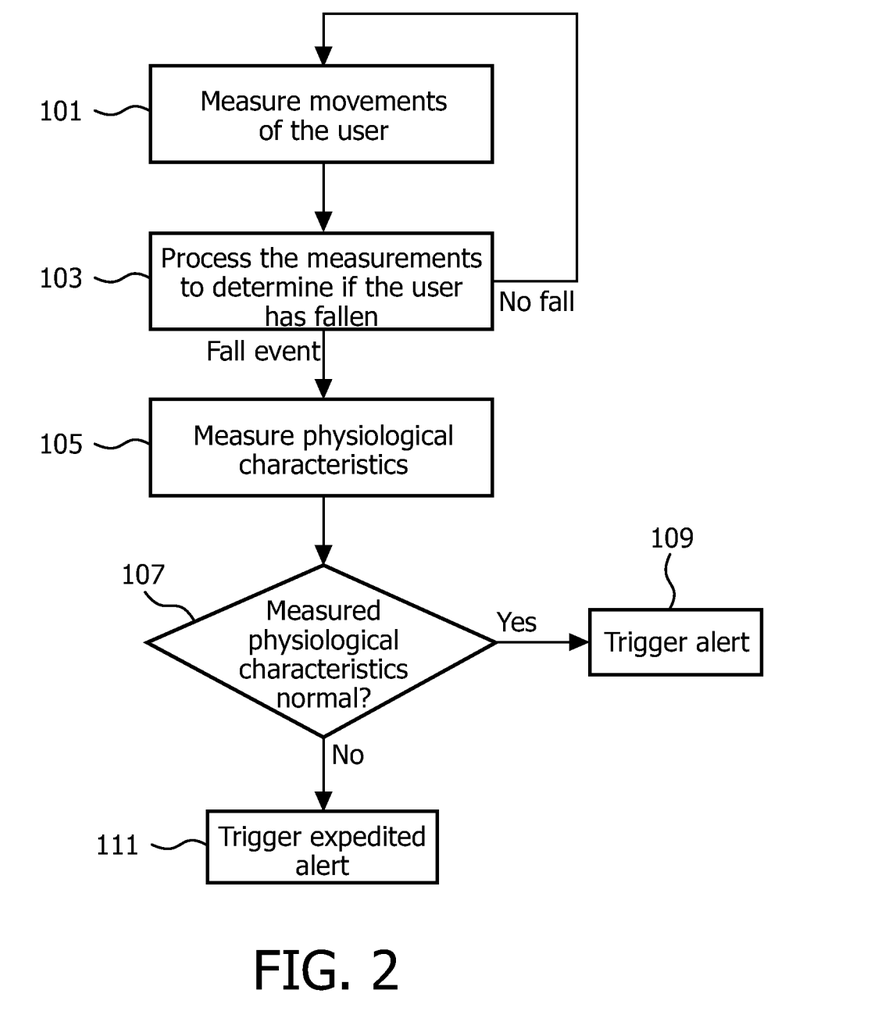
FIG. 2 is a flow chart illustrating an exemplary method of operating a fall detector or fall detection system according to the invention.

A method of operating the fall detector 2 is shown in FIG. 2. It will be appreciated that the method described can easily be adapted to the fall detection system described above. In the first step, step 101, the movements of the user are measured. In particular, measurements of the movement of the user are collected by movement sensor 4 (i.e. accelerometer 4) and any other sensor 13 that is present in the fall detector 2. These measurements are provided to the processor 6 where they are processed to determine if the user has fallen (step 103).

A fall can be broadly characterized by, for example, a change in altitude of around 0.5 to 1.5 meters (the range may be different depending on the part of the body that the fall detector 2 is to be worn and the height of the user), culminating in a significant impact, followed by a period in which the user does not move very much. Another example characteristic can be the presence of a substantial vertical (downwards) velocity. Thus, in order to determine if a fall has taken place, the processor 6 can process the measurements to extract values for features including a change in altitude (which is usually derived from measurements from a pressure sensor 13, but can also or alternatively be derived from the measurements from the accelerometer 4), a maximum activity level (i.e. an impact) around the time that the change in altitude occurs (typically derived from the measurements from the accelerometer 4) and a vertical velocity. Other features can further improve the reliability of the detection algorithm. For example, a change in orientation coinciding with the height change increases the likelihood that the user has fallen. This orientation change can be measured using the accelerometer 4 and/or alternatively using a magnetometer or gyroscope.

A fall event may be detected where some or all of the required features (such as height change, impact, vertical velocity and orientation change) are present in the movement measurements. Alternatively, the values for the extracted features can be combined (possibly using weightings for each extracted feature) in order to determine if the user has fallen, with a strong presence for one or more of the extracted features (i.e. a particularly large impact) compensating for a weaker presence of another extracted feature (i.e. a relatively small height change).

The analysis performed by the processor 6 in step 103 in detecting whether a fall event has occurred will not be described in further detail herein, but those skilled in the art will be aware of various algorithms and techniques that can be applied to determine whether a user may have suffered a fall from accelerometer measurements and/or measurements from other types of movement sensors.

In step 103, the processor 6 can also extract a value for the period in which the user is relatively inactive following the impact from the movement sensor measurements. As with the other features described above, this value can typically be derived from the measurements from the accelerometer 4. Alternatively, or in addition, the processor 6 can determine from the movement sensor measurements whether the user has got up after the fall, which includes standing up or otherwise returning to an upright posture, after a detected impact and/or height change. Exemplary processing steps that can be used to determine whether the user has got up are described in more detail with reference to FIG. 3.

If no fall has occurred (step 103), then the process returns to step 101 and monitoring of the user continues.

In a conventional fall detector, an alert would be initiated on detection of a fall event in step 103, or a revocation period would be started in order to allow time for the user to get up after the fall event.

However, as indicated above, any delay in triggering an alert and summoning help to the user can be serious if the detected fall has been caused by some underlying health-related issue, such as a stroke or a cardiac arrest. Therefore, the invention provides that at least one physiological characteristic of the user is measured when a fall or a possible fall has been detected, and this measurement is used to determine whether to expedite an alert that the user has fallen and requires help.

Thus, if a fall or a possible fall is detected in step 103, then measurements of one or more physiological characteristics of the user are made (step 105).

Where the fall detector 2 comprises specific physiological characteristic sensors 16 (whether within a single housing or provided in a separate component), then step 105 can comprise activating those sensors 16 in response to the detected fall or possible fall and making the appropriate measurements. Alternatively, where one of the movement sensors (such as the accelerometer 4) is used to measure the physiological characteristic(s), the processor 6 can extract the appropriate characteristic(s) from movement sensor measurements collected immediately before, during and/or after the detected fall. Those skilled in the art will be aware of various algorithms and techniques that can be used to extract physiological characteristic measurements using signals from movement sensors, such as an accelerometer 4, and they will therefore not be described in any further detail herein.

In a preferred embodiment, as the physiological characteristic sensor(s) 16 or the specific processing performed by the processor 6 to determine the physiological characteristics are only used when a fall or a possible fall have been detected, the power consumption of the processor 6 and thus the fall detector 2 during non-fall times can be minimized. As the analysis in step 103 is typically performed by the processor 6 substantially in real time or with only a small delay, the physiological characteristics can be determined shortly after a fall event has actually occurred.

In an alternative embodiment, the physiological characteristic sensor(s) 16 can be used as part of a monitoring system to periodically measure the physiological characteristics of the user (for example they can take measurements every 15 minutes). In this case, the detection of a fall event in step 103 results in the processor 6 requesting the measurement of a physiological characteristic by the physiological characteristic sensor(s) 16 straight after the fall event has been detected, regardless of the normal monitoring regime of the physiological characteristic sensor(s) 16.

Then, in step 107, it is determined if the physiological characteristics measured in step 105 are normal. This step can comprise comparing each physiological characteristic measurement to an appropriate threshold value or range of values representing a normal value for that physiological characteristic. It will be appreciated that the absence of a physiological characteristic (for example no detectable heart rate/pulse or breathing rate in the movement sensor measurements and/or the physiological sensor measurements) is also classed as 'not normal'. In addition, or alternatively, the regularity and form of the pattern of the physiological characteristic (e.g. pulse or breathing) that appears in the measurement can be assessed.

As an example, a threshold value for a heart rate can be 30 beats per minute, with any measured value below that being considered abnormal. Alternatively, a normal range for heart rate can be between 30-90 beats per minute, with any measured value falling outside that range being considered abnormal. A typical respiration rate is 16 breaths per minute, and a normal value or normal range can be set accordingly. Likewise, a normal temperature is 37° C., and a normal range can be set accordingly Skin conductivity differs among people and depends, among other things, on skin type. Abnormality, therefore, is detected as a deviation from the normal values for that person.

Those skilled in the art will be aware of suitable thresholds or ranges that can be used to determine whether different physiological characteristic measurements are normal. It will be appreciated that falling is a stressful event for the person involved, which will have an influence on various vital signs (such as the heart rate, breathing rate, skin conductivity, etc.), and this fact can be taken into account when setting the normal values or ranges for the physiological characteristics.

It will also be appreciated that the normal values or range of values can be set to the same values for each user of the fall detector 2, or they can be calibrated to individual users.

If the measured physiological characteristics are normal, then an alert that the user has fallen can be initiated (step 109). This alert is triggered according to the normal alert procedure for the fall detector 2. As described above, the alert can comprise the placing a call over a wired or wireless telephone network (or other type of network, such as the Internet) to a call centre or nominated person, transmitting data (including the sending of an SMS message) indicating that the user has fallen to a call centre, activating an audible alarm unit 8 in the detector 2 or another device, such as a base unit for the fall detector 2, or any other suitable type of alert. In an embodiment where a revocation period is used (as described with reference to FIG. 3 below), the normal alert procedure can comprise testing to determine if the user gets up within the revocation period, and if not, triggering an alert (such as placing a call).

If it is determined in step 107 that one or more of the measured physiological characteristics are not normal, then the user may require assistance more urgently than another user who has fallen but whose physiological characteristics are normal, and an expedited alert procedure can be triggered (step 111). In this procedure, the alert can be expedited in one or more of the exemplary ways discussed above. For example, in an embodiment where a revocation period is used (as described below), the alert can be triggered as soon as the abnormal physiological characteristic is measured, i.e. without waiting for the revocation period to expire. The alert triggered in this case can be identical to that triggered in the normal alert procedure (step 109), however it is 'expedited' in the sense that it is triggered earlier than in the normal alert mode.

In some embodiments, the call placed in step 109 or step 111 can be 'labeled' by the fall detector 2 in response to the determination in step 107 in order to appropriately prioritize the call at the call centre (and thus expedite the handling of the call, as required). For example, if the user's heart rate is outside the normal range, then the call will be triggered and the signaling provided to the call centre can indicate the status of the user (i.e. abnormal heart rate, urgent help required, etc), allowing the call to be placed at the top of any queue (or in a different 'higher priority' queue) at the call centre. If the user's heart rate is within a normal range, the signaling can indicate the 'normal' heart rate status of the user or the measured heart rate itself, and the call can be queued in the normal way at the call centre.

This 'labeling' can be implemented using a bit string in a message that is sent to the call centre. The 'value' of the bit string can be determined, for example, based on the results of steps 103 and 107. The bit string could also include one or more bits indicating whether a user has manually pressed a help button.

This 'labeling' can also be used to make the operator at the call centre aware that they might not receive any response when attempting to communicate with the user and that assistance from the emergency services may be required.

It will be appreciated that the physiological characteristics that can be measured by the fall detector 2 can depend on where on the body of the user the fall detector 2 is to be worn. For example, a fall detector 2 can typically be worn as a pendant around the neck, on the wrist or at the waist.

When implemented as a pendant, the detector 2 can measure heart rate and/or respiration rate using the accelerometer 4, when, for example, the user is sitting in a chair or standing upright. Provided the pendant is worn beneath the user's clothes, it should still be in contact with the user after a fall and can still be used to measure the heart rate and/or respiration rate.

When implemented as a wrist-worn fall device, the fall detector 2 can include sensors 16 for measuring skin conductivity and blood pressure. In addition, heart rate can be measured, for example using a photoplethysmograph (PPG).

When implemented as a waist-worn device, the fall detector 2 can measure heart rate and/or respiration rate, for example using the accelerometer 4.

It will be appreciated that expediting an alert according to the invention results in assistance being provided more rapidly to the user than would be the case for a normal (non-expedited) alert. Thus, a fall detector according to the invention could be understood as having two alert 'modes'—a normal alert mode that is used when the physiological characteristics of the user are normal, and an expedited alert mode that is used when the physiological characteristics of the user are not normal and which results in assistance being provided to the user more quickly than with the normal alert.

Figure 3:
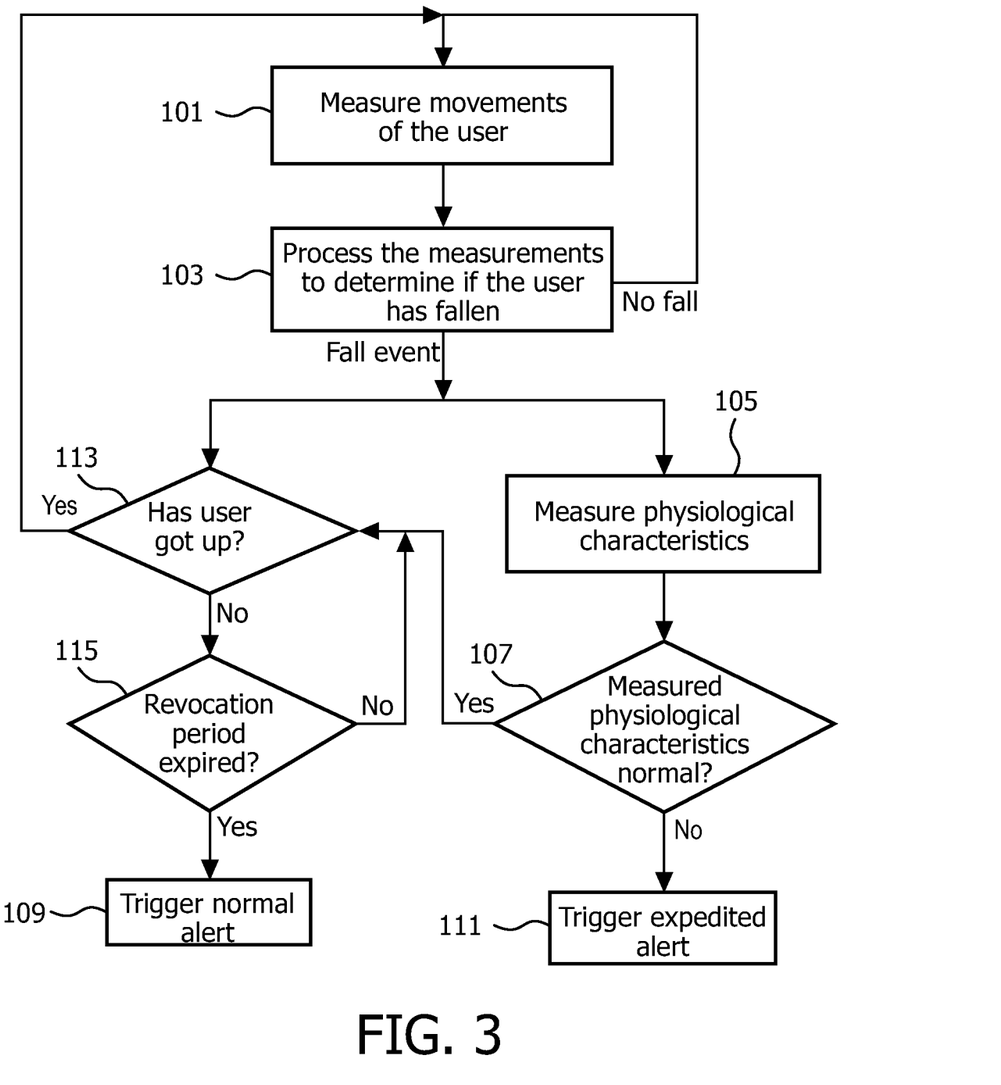
FIG. 3 is a flow chart illustrating a method of operating a fall detector or fall detection system according a specific embodiment of the invention in which a revocation period is used.

A method of operating a fall detector that uses a revocation period is shown in FIG. 3. Steps in FIG. 3 that correspond to those described above for FIG. 2 are given the same reference numerals. The method in FIG. 3 mostly corresponds to the method in FIG. 2, with the difference that, when a fall event is detected (step 103), testing for a revocation period starts (steps 113 and 115) alongside the measurement of one or more physiological characteristics in step 105, and, if the measured physiological characteristics are normal, the processor 6 awaits the expiry of the revocation period before triggering a normal alert (step 109). If the measured physiological characteristics are not normal, the processor triggers an expedited alert as described above (step 111) regardless of whether the user has got up or whether the revocation period has expired. As indicated above, it will be appreciated that the alerts triggered in steps 109 and 111 can be the same (e.g. the placing of a call to a call centre), with the alert in step 111 being 'expedited' in the sense that it is not necessary for the revocation period to expire before triggering the alert (as with the normal alert in steps 113, 115 and 109). However, it will also be appreciated that in addition to initiating the alert before the revocation period has expired, that alert can be expedited in one or more of the ways described above.

In particular, if a fall event is detected in step 103, the processor 6 can start a timer and wait until the expiry of a predetermined revocation period before triggering a normal alert (which can include activating an audible alarm, placing a call to a call centre or nominated person, sending data (including sending an SMS message) indicating the user's situation to a call centre, etc.). This revocation period can typically be 30 seconds long, although other durations can be used. During this revocation period, the processor 6 monitors the movements and/or orientation of the user to determine if the user has stood up or otherwise returns to being upright following the fall or possible fall. This corresponds to step 113 in FIG. 3.

Intermittently or periodically throughout the revocation period the processor 6 checks whether the user has got up (e.g. stood up or has returned to being upright) after the detected fall (step 113), and if the user has not got up, the processor 6 continues monitoring the user until the revocation period expires (step 115).

In an exemplary embodiment, the processing used to identify whether the user has got up comprises the following steps:

- identifying a part of the accelerometer measurement within a time window (e.g. 3 seconds) after a detected impact in which the difference between the maximum and minimum value of the absolute acceleration over a time period (e.g. 0.5 seconds) is less than a threshold (e.g. 0.4 m/s$^2$). A height measurement is taken for that time period (by for example the pressure sensor) and the minimum in these measurements is denoted the 'lower height'.
- if such a part of the measurement is found, the state is defined as "lying". Otherwise, the minimum height as measured by the pressure sensor is determined and the state is defined as "moving".
- for as long as the state "lying" persists, the test for the difference in the maximum and minimum values of the absolute acceleration being within 0.4 m/s$^2$ is performed. If not, the state is defined as "moving". Meanwhile, if a lower height is measured, that value is taken as the lower height. If the state "lying" persists for a time period following the impact (e.g. 30 seconds), no revocation is concluded (i.e. the decision in step 115 is 'Yes').
- If the state is "moving", it is tested whether the accelerometer 4 is more strongly moving (for example if the variance in acceleration passes a threshold and/or an orientation change passes a threshold). If found, the state is defined as "standing". If this is not found within a time period (e.g. 30 seconds) since impact, no revocation is concluded (i.e. the decision in step 115 is 'Yes'). Meanwhile, if a lower height is measured, that value is taken as the lower height.
- If the state is "standing", it is tested whether the current height is higher than a predetermined amount (e.g. 80 cm) above the current value for the lower height. If so and it is within a predetermined period after the impact (e.g. 30 seconds), the fall is revoked and no alert is issued (i.e. the decision in step 113 is 'Yes'). If not and the predetermined period after impact (e.g. 30 seconds) has passed, no revocation is concluded (i.e. the decision in step 115 is 'Yes'). Meanwhile if a lower height is measured, that value is taken as the lower height.

If the revocation period expires without the user getting up, then a (normal) alert is triggered (step 109). As indicated above, this could comprise the processor 6 activating an audible alarm 8 in the fall detector 2, placing an emergency call or sending data (including sending an SMS message) to a call centre or nominated person over a telephone network (either wirelessly from the fall detector 2 or through a fixed line connection associated with a base unit for the fall detector 2).

However, if the user does get up (i.e. stand up or return to being upright) before the revocation period expires (step 113), then it is assumed that the user is okay (i.e. either they did not actually fall, or the fall was not particularly severe and they are now able to summon help manually using the help button or other means, if required). Therefore, the method returns to step 101 and the monitoring of the movements of the user continues.

It will be appreciated that in the method illustrated in FIG. 3, the revocation period and testing to determine if the user has got up (steps 113 and 115) is performed alongside the measurement of the physiological characteristics (step 105).

In an alternative implementation, the revocation period and testing to determine if the user has got up is initiated only if it is determined in step 107 that the physiological characteristic(s) are normal.

As described above, a fall detection algorithm tests for several features, such as height drop, impact and orientation change, and typically all features are required to be identified in the movements of the user in order for a fall to be detected, although the strong presence of one or more features may compensate for a weak presence of another. However, in cases where a user falls as a result of, for example a stroke or cardiac arrest, the fall can be more of a gentle collapse without a fast height drop and a strong impact with the ground. The usual fall detection processing might be set up in a way that leads to these fall events being classified as non-falls in order for the false-alarm rate of the fall detector 2 to remain at a low level. Thus, these fall events would not be classed as falls (resulting in a 'no fall' output in step 103) and the method would return to step 101.

However, in a further embodiment of the invention, the fall detector 2 can be provided with a "soft fall" mode of operation in which, when a possible fall event occurs where one or more (but not necessarily all) of the required features of a fall are identified in the movement signal, a measurement of the physiological characteristic(s) of the user can be made by the fall detector 2 (step 105), and that measurement used to determine whether the fall event may have been an actual fall (or whether the user needs help regardless) and thus trigger an expedited alert (step 111). In this "soft fall" mode, if it is determined that the physiological characteristic is not normal then an expedited alert will be issued (as per step 111). However, a determination in step 107 that the physiological characteristic measurement is normal will result in the method returning to step 101 rather than proceeding to step 109 (the issue of a normal alert). In this mode, the alert in step 111 is "expedited" in the sense that an alert as described above (including a 'normal' alert) is initiated automatically when it would not otherwise have been initiated by the fall detector 2 at all (but where, for example, it could have been subsequently issued by a user manually pressing a help button). Providing a fall detector 2 with this "soft fall" mode of operation is one way of increasing the detection rate of failures in the user's vital body systems, while also avoiding the need for continuous monitoring of the physiological characteristics by the fall detector 2 (and thereby avoiding the increase in power consumption that this would entail).

There is therefore provided a fall detector and a method of operating the same in which the time taken to get help to a user who has suffered a fall can be reduced if that user is urgently in need of help.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of operating a fall detector, the method comprising:
    on detecting a fall event by a user of the fall detector, measuring at least one physiological characteristic of the user;
    using the measurement of the at least one physiological characteristic to determine whether to expedite an alert that the user has fallen by: determining if the measurement of the at least one physiological characteristic deviates from a normal value for the at least one physiological characteristic; and
    automatically expediting, by a processor, an alert that the user has fallen by triggering an alert before an expiry of a revocation period if the at least one physiological characteristic deviates from a normal value for the at least one physiological characteristic.

2. The method as claimed in claim 1, further comprises: initiating a non-expedited alert that the user has fallen if it is determined that the user has not got up within a predetermined time period after the detected fall event.

3. The method as claimed in claim 1, wherein the step of determining if the measurement of the at least one physiological characteristic deviates from a normal value for the at least one physiological characteristic comprises comparing the measurement of the at least one physiological characteristic to a threshold value or a normal range of values for the at least one physiological characteristic.

4. The method as claimed in claim 1, wherein the normal value for the at least one physiological characteristic is user-dependent.

5. The method as claimed in claim 1, the method further comprising the steps of:
    measuring the movements of the user; and
    analyzing the measured movements to identify one or more movements indicative of a fall by the user.

6. The method as claimed in claim 5, wherein the measured movements are further analyzed to obtain the measurement of the at least one physiological characteristic of the user.

7. The method as claimed in claim 5, wherein the step of measuring at least one physiological characteristic of the user comprises using a sensor different to that used to measure the movements of the user.

8. The method as claimed in claim 5, wherein the one or more movements consistent with a fall are selected from an impact, a change in height of the user, a vertical velocity and a change in orientation of the user.

9. The method as claimed in claim 1, wherein an alert comprises at least one of an audible alarm, a call to a call center, emergency service or nominated recipient or sending data to a call center, emergency service or nominated recipient.

10. The method as claimed in 1, wherein expediting an alert comprises one or more of:
    labeling a call or message as high priority such that queuing of the call or message at a recipient is expedited compared to a non-expedited alert, initiating an alert through a higher priority or higher bandwidth channel in a network than a non-expedited alert, and initiating an alert to an emergency service instead of, or in addition to, a call center associated with the fall detector.

11. The method as claimed in claim 1, wherein the at least one physiological characteristic is selected from heart rate, heart rate variability, respiration rate, respiration rate variability, body temperature, skin conductivity and blood pressure.

12. A computer program product comprising computer readable code embodied therein, the code being configured such that, on execution by a suitable computer or processor, the computer or processor is caused to perform the method as claimed in claim 1.

13. An apparatus, comprising:
a processing unit that is configured to:
  determine a measurement of at least one physiological characteristic of a user of a fall detector on detecting a fall event by the user; and
  use the measurement of the at least one physiological characteristic to determine whether to expedite an alert that the user has fallen by:
    determining if the measurement of the at least one physiological characteristic deviates from a normal value for the at least one physiological characteristic;
  expediting an alert that the user has fallen if the at least one physiological characteristic deviates from a normal value for the at least one physiological characteristic; and
  issuing a non-expedited alert that the user has fallen if the at least one physiological characteristic does not deviate from a normal value for the at least one physiological characteristic.

14. The method as claimed in claim 1, further comprises:
initiating a non-expedited alert that the user has fallen if it is determined that the user has not got up within a predetermined time period after the detected fall event and the at least one physiological characteristic does not deviate from the normal value for the at least one physiological characteristic.

15. The method as claimed in claim 1, further comprises:
initiating no alert if it is determined that the user has gotten got up within a predetermined time period after the detected fall event.

16. The method as claimed in claim 1, further comprises:
initiating no alert if it is determined that the user has gotten got up within a predetermined time period after the detected fall event and the at least one physiological characteristic does not deviate from the normal value for the at least one physiological characteristic.

17. A method, comprising:
expediting, with a processor, issuance of an automatically generated alert that a user has fallen if at least one physiological characteristic, of the user measured after a fall event has been determined, deviates from a normal value for the at least one physiological characteristic; and
issuing, with the processor, an automatically generated non-expedited alert that the user has fallen if the at least one physiological characteristic does not deviate from the normal value for the at least one physiological characteristic.

18. The method as claimed in 17, further comprises:
initiating the non-expedited alert that the user has fallen if it is determined that the user has not got up within a predetermined time period after the detected fall event.

19. The method as claimed in claim 17, further comprises:
initiating no alert if it is determined that the user has gotten got up within a predetermined time period after the detected fall event.

20. The method as claimed in claim 17, further comprises:
initiating no alert if it is determined that the user has gotten got up within a predetermined time period after the detected fall event and the at least one physiological characteristic does not deviate from the normal value for the at least one physiological characteristic.

* * * * *